(12) United States Patent
Schwerin et al.

(10) Patent No.: US 6,897,342 B2
(45) Date of Patent: May 24, 2005

(54) METHOD FOR PRODUCING ALDEHYDES

(75) Inventors: Albrecht Schwerin, Duesseldorf (DE); Gerrit Pelzer, Duesseldorf (DE); Lothar Friesenhagen, Duesseldorf (DE); Bernhard Gutsche, Hilden (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 10/311,838

(22) PCT Filed: Jun. 19, 2001

(86) PCT No.: PCT/EP01/06859

§ 371 (c)(1),
(2), (4) Date: Jul. 11, 2003

(87) PCT Pub. No.: WO02/00581

PCT Pub. Date: Jan. 3, 2002

(65) Prior Publication Data

US 2004/0002620 A1 Jan. 1, 2004

(30) Foreign Application Priority Data

Jun. 28, 2000 (DE) .......................................... 100 44 809

(51) Int. Cl.⁷ .............................................. C07C 45/00
(52) U.S. Cl. ..................................... 568/471; 568/485
(58) Field of Search .................................. 568/471, 485

(56) References Cited

U.S. PATENT DOCUMENTS 4,891,446 A * 1/1990 Slaugh 5,227,530 A * 7/1993 Satek et al.

FOREIGN PATENT DOCUMENTS

| DE | 23 58 254 A1 | * | 6/1975 |
| EP | 0 320 074 B1 | * | 6/1989 |
| JP | 50 130708 | * | 10/1975 |
| RO | 0111820 | * | 2/1997 |
| SU | 345115 | * | 11/1970 |
| SU | 572450 | * | 12/1977 |

OTHER PUBLICATIONS

Subject Index "Applied Catalysis A: General 197", Subject Index, (2000), pp 319–324.*
C. Bilgrien et al., "The Selective Oxidation of Primary Alcohols to Aldehydes by $O_2$ Employing a Trinuclear Ruthenium Carboxylate Catalyst", J. Am. Chem. Soc., 1987, 109, pp 3786–3787.*
J. S. Cha et al., "One–pot Conversion of Carboxylic Acids to Aldehydes Through Treatment of Acyloxy–9–borabicyclo [3.3.1] Nonanes with Lithium 9–boratabicyclo [3.3.1] Nonane", Tetrahedron Lett. 28, 1987, pp 4575–7578.*

* cited by examiner

*Primary Examiner*—Johann Richter
*Assistant Examiner*—Sikarl A. Witherspoon
(74) *Attorney, Agent, or Firm*—Aaron R. Ettelman; Daniel S. Ortiz; Steven J. Trzaska

(57) ABSTRACT

A process for making aldehydes involving: (a) providing a fatty alcohol; (b) providing an oxidic copper/zinc catalyst; and (c) continuously dehydrogenating the fatty alcohol, in the presence of the oxidic copper/zinc catalyst, at a temperature of from about 200 to 280° C. and a pressure of from about 10 mbar to 1 bar.

9 Claims, No Drawings

METHOD FOR PRODUCING ALDEHYDES

BACKGROUND OF THE INVENTION

This application is a 371 of PCT/EP01/06859 filed Jun. 19, 2001.

This invention relates generally to perfumes and, more particularly, to a new process for the production of fatty aldehydes.

Lower aldehydes such as 1-octanal or 1-decanal, for example, are sought-after raw materials for the perfume industry. Their production from fatty alcohols, for example by oxidation with hypochlorite in the presence of 4-methoxy-2,2,6,6-tetramethyl piperidin-1-yloxyl ("Tempo"), is known from the prior art. The oxidation of the alcohols with air can be carried out in the presence of ruthenium or platinum catalysts. In addition, unsaturated alcohols can be isomerized to aldehydes under the influence of iron pentacarbonyl. The aldehydes are obtained from fatty acids by hydrogenation on oxidic copper catalysts of the Adkins type or by reaction with per acids in the presence of titanium (IV) oxide. RO 0111820 (Comb. Chim. Rimnicu Vilcea) reports on the use of heterogeneous oxidic copper catalysts for the dehydrogenation of fatty alcohols. Iron-doped copper catalysts are proposed for the same purpose in EP 0320074 A1 (Engelhard). A classic method is the Rosenmund reaction in which acid chlorides are hydrogenated to the corresponding aldehydes on Lindlar catalysts. Reference is made in this connection to the overview articles in J. Am. Chem. Soc. 109, 3786 (1987), J. Org. Chem. 52, 2259 (1987) and Tetrahedron Lett. 28, 4575 (1987).

Unfortunately, the known processes have the disadvantage that they are equipment-intensive, give low yields and/or are characterized by unsatisfactory selectivities. Accordingly, the problem addressed by the present invention was to provide a new process which would reliably avoid the above-mentioned disadvantages of the prior art.

DESCRIPTION OF THE INVENTION

The present invention relates to a process for the production of aldehydes in which fatty alcohols are continuously dehydrogenated in the presence of oxidic copper/zinc catalysts at temperatures of 200 to 280° C. and under pressures in the range from 10 mbar to 1 bar.

It has surprisingly been found that, by using the catalysts mentioned, fatty alcohols can be continuously dehydrogenated to fatty aldehydes in yields of over 60% of the theoretical and with selectivities of over 90% of the theoretical.

Fatty Alcohols

Suitable starting materials for the process according to the invention are linear or branched, saturated or unsaturated primary alcohols which, in the interests of simplicity, are collectively referred to as fatty alcohols and which preferably correspond to formula (I):

$$R^1OH \tag{I}$$

where $R^1$ is a linear or branched, saturated or unsaturated alkyl and/or alkenyl group containing 6 to 22, preferably 8 to 12 and more particularly 8 to 10 carbon atoms. Typical examples are caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and the technical mixtures thereof obtained, for example, in the high-pressure hydrogenation of technical methyl esters based on fats and oils or aldehydes from Roelen's oxo synthesis and as monomer fraction in the dimerization of unsaturated fatty alcohols. Caprylic alcohol (1-octanol), 2-ethylhexanol and capric alcohol (1-decanol) and mixtures thereof are preferably used.

Synthesis

The fatty aldehydes are preferably produced in a shaft reactor with a fixed catalyst bed. The oxidic copper/zinc catalysts are commercial Adkins catalysts, i.e. solids with a spinel structure which preferably contain chromium, cadmium, cerium, barium, silicon and/or aluminium as other metal components. Basic copper/zinc/aluminum oxides are particularly preferred. The reaction normally takes place at temperatures of 200 to 280° C. and preferably at temperatures of 240 to 260° C. The dehydrogenation is carried out either in the absence of pressure or under a reduced pressure preferably in the range from 20 to 40 mbar. The liquid hourly space velocity (LHSV) is in the range from 1 to 3 and preferably in the range from 1.1 to 2.6 $h^{-1}$. The yield of fatty aldehydes is of the order of at least 60% and preferably 65 to 70% of the theoretical while selectivity is at least 90% and preferably 95 to 98%. It is advisable to carry out the dehydrogenation in the presence of nitrogen as carrier gas.

EXAMPLES

In a continuous pressure reactor with a fixed catalyst bed, fatty alcohols were dehydrogenated to the corresponding aldehydes at a temperature of 250° C. and under pressures of 20 mbar to normal pressure. The test results are set out in Table 1. The aldehydes were obtained in yields of 60 to 70% and with selectivities of more than 90% of the theoretical.

TABLE 1

| Continuous dehydrogenation of fatty alcohols | | | | | |
|---|---|---|---|---|---|
| Test parameter | 1 | 2 | 3 | 4 | 5 |
| Educt | 1-Octanol | 1-Decanol | 1-Decanol | 1-Octanol | 1-Octanol |
| Product | 1-Octanal | 1-Decanal | 1-Decanal | 1-Octanal | 1-Octanal |
| Catalyst metal | Cu/Zn/Al[1)] | Cu/Zn/Al[1)] | Cu/Zn | Cu/Zn | Cu/Si |
| LHSV [$h^{-1}$] | 1.1 | 1.1 | 2.6 | 1.8 | 0.7 |
| Temperature [° C.] | 250 | 250 | 250 | 250 | 250 |
| Pressure [mbar] | 1000 | 20 | 42 | 40 | 17 |
| Conversion educt [% of th.] | 73 | 61 | 69 | 67 | 88 |
| Yield product [% of th.] | 66 | 57 | 67 | 64 | 84 |
| Selectivity [% of th.] | 90 | 93 | 97 | 97 | 95 |

[1)]Leuna catalyst 1962

What is claimed is:

1. A process for making aldehydes comprising:
   (a) providing a fatty alcohol;
   (b) providing an oxidic copper/zinc catalyst; and
   (c) continuously dehydrogenating the fatty alcohol, in the presence of the oxidic copper/zinc catalyst, at a temperature of from about 200 to 280° C. and a pressure of from about 10 mbar to 1 bar.

2. The process of claim 1 wherein the oxidic copper/zinc catalyst contains a metal component selected from the group consisting of chromium, cadmium, cerium, barium, silicon, aluminium, and mixtures thereof.

3. The process of claim 1 wherein the fatty alcohol is continuously dehydrogenated at a temperature of from about 240 to 260° C.

4. The process of claim 1 wherein the fatty alcohol is continuously dehydrogenated at a pressure of from about 20 to 40 mbar.

5. The process of claims wherein the fatty alcohol is continuously dehydrogenated at a liquid hourly space velocity of from about 1 to 3 $h^{-1}$.

6. The process of claim 1 wherein the fatty alcohol is continuously dehydrogenated using nitrogen as a carrier gas.

7. The process of claim 1 wherein the aldehydes are made in yields in excess of 60% of theoretical.

8. The process of claim 1 wherein the aldehydes are made in yields of from about 65 to 70% of theoretical.

9. The process of claim 1 wherein the fatty alcohol is selected from the group consisting of caprylic alcohol, 2-ethylhexanol, capric alcohol and mixtures thereof.

* * * * *